United States Patent
Ganey et al.

(10) Patent No.: US 11,077,148 B2
(45) Date of Patent: Aug. 3, 2021

(54) ACELLULAR BIOLOGIC COMPOSITION AND METHOD OF MANUFACTURE

(71) Applicant: Vivex Biologics Group, Inc., Atlanta, GA (US)

(72) Inventors: Timothy Ganey, Tampa, FL (US); Wendy W. Weston, Miami, FL (US); Gaëtan Jean-Robert Delcroix, Miami, FL (US)

(73) Assignee: Vivex Biologics Group, Inc., Atlanta, GA (US)

( * ) Notice: Subject to any disclaimer, the term of this patent is extended or adjusted under 35 U.S.C. 154(b) by 24 days.

(21) Appl. No.: 15/950,365

(22) Filed: Apr. 11, 2018

(65) Prior Publication Data

US 2018/0228848 A1    Aug. 16, 2018

Related U.S. Application Data

(62) Division of application No. 14/810,003, filed on Jul. 27, 2015.

(60) Provisional application No. 62/194,574, filed on Jul. 20, 2015.

(51) Int. Cl.
| | | |
|---|---|---|
| *A61K 35/50* | (2015.01) | |
| *C12N 5/00* | (2006.01) | |
| *C12N 5/073* | (2010.01) | |

(52) U.S. Cl.
CPC ............... *A61K 35/50* (2013.01); *C12N 5/00* (2013.01); *C12N 5/0605* (2013.01)

(58) Field of Classification Search
None
See application file for complete search history.

(56) References Cited

U.S. PATENT DOCUMENTS

| | | | |
|---|---|---|---|
| 5,837,539 A | 11/1998 | Caplan et al. | |
| 7,029,839 B2 | 4/2006 | Toledo-Pereyra | |
| 2005/0013872 A1* | 1/2005 | Freyman | A61K 35/28 424/549 |
| 2007/0191963 A1* | 8/2007 | Winterbottom | A61F 2/28 623/23.5 |
| 2008/0181935 A1* | 7/2008 | Bhatia | A61K 38/39 424/443 |
| 2010/0111897 A1* | 5/2010 | Katz | A61K 38/18 424/85.2 |
| 2010/0228335 A1 | 9/2010 | Schorgl | |
| 2013/0344162 A1* | 12/2013 | Morse | A61K 35/50 424/582 |
| 2014/0065240 A1* | 3/2014 | Mitsialis | A61K 35/28 424/577 |
| 2015/0024011 A1* | 1/2015 | Lim | A61K 8/14 424/400 |

OTHER PUBLICATIONS

Brockbank et al., Chapters: Tissue Preservation, Advances in Biopreservation, Jun. 2006, pp. 157-196; retrieved from the internet: www.andrew.cmu.edu/user/yr25/TaylorPublications/MJTaylor108.pdf.*
Schenke-Layland et al., Ann. Thorac Surg, 2006; 81: 918-927.*
Brockbank et al, Cryopreservation Guide, Thermo Scientific, 2007, retrieved from the internet:https://www.thermofisher.co.nz/Uploads/file/Scientific/Applications/Equipment-Furniture/Cryopreservation-Guide.PDF.*
ATCC, SOP: Thawing, Propagating and Cryopreserving Protocol for NCI-PBCF-CRL 1619, Sep. 12, 2013; retreived from the internet: https://physics.cancer.gov/docs/bioresource/skin/NCI-PBCF-CRL1619_A-375_SOP-508.pdf.*
Donnenberg et al., Regen Med. Nov. 2011; 6(6): 701-706.*
Kadiu et al., The Journal of Immunology, 2012; 189:744-754.*
Lobb et al., Journal of Extracellular Vesicles, 2015, vol. 4:27031, pp. 1-11, published Jul. 17, 2015.*
Lorincz et al., Journal of Extracellular Vesicles, 2014, pp. 1-8.*
Xu et al., PLOS One, Dec. 11, 2014, pp. 1-19.*
Yamaguchi et al., British Journal of Dermatology 2004; 151: 1019-1028.*
Salomon et al., PLOS One, Jul. 2013, vol. 8, Issue 7, e68451, pp. 1-24 (Year: 2013).*
Van Deun et al., Journal of Extracellular Vesicles, published Sep. 18, 2014, vol. 3: 24858, pp. 1-14 (Year: 2014).*
Dietrich et al., GEA, Fundamentals of Pharmaceutical Freeze Drying, Nov. 2014, 9 pages (Year: 2014).*
Li et al., Immunosuppressive Factors Secreted by Human Amniotic Epithelial Cells, Investigative Ophthalmology & Visual Science, Mar. 2005, vol. 46, No. 3, pp. 900-907.
Luo et al., Human Villous Trophoblasts Express and Secrete Placenta-Specific MicroRNAs into Maternal Circulation via Exosomes, Biology of Reproduction, vol. 81, pp. 717-729 (2009).
Sheller et al., Amnion-Epithelial-Cell Derived Exosomes Demonstrate Physiologic State of Cell under Oxidative Stress, PLOS One, Jun. 22, 2016, pp. 1-25.

* cited by examiner

*Primary Examiner* — Scott Long
*Assistant Examiner* — Evelyn Y Pyla
(74) *Attorney, Agent, or Firm* — David L. King

(57) ABSTRACT

A biological composition has a mixture of mechanically selected allogeneic biologic material derived from placental tissue. The mixture has non-whole cellular components including vesicular components and active and inactive components of biological activity, cell fragments, cellular excretions, cellular derivatives, and extracellular components. The mixture including non-whole cell fractions including one or more of exosomes, transcriptosomes, proteasomes, membrane rafts, lipid rafts. The mixture is compatible with biologic function.

14 Claims, 4 Drawing Sheets
(4 of 4 Drawing Sheet(s) Filed in Color)

ACELLULAR BIOLOGIC COMPOSITION AND METHOD OF MANUFACTURE

RELATED APPLICATIONS

This application is a division of co-pending application U.S. Ser. No. 14/810,003 filed on Jul. 27, 2015 entitled, "Acellular Biologic Composition And Method Of Manufacture".

TECHNICAL FIELD

This invention is a tissue regenerative biological composition. More specifically, a composition at least in part formed from placental contents and a method of manufacture and use of said composition with an acellular mixture.

BACKGROUND OF THE INVENTION

In the area of tissue regeneration or repair, the use of stem cell therapy has been widely touted as essential to sustaining regenerative inertia in tissue repair and guiding sufficient metabolic inertia to supplement matrix deposition and organ consolidation.

Often, these inventions describe isolating the stem cells, purifying and culturally expanding mesenchymal stem cells. In U.S. Pat. No. 5,837,539, entitled "Monoclonal Antibodies For Human Mesenchymal Stem Cells", Arnold Caplan et al. reported that the cells are preferably culturally expanded, but suggest it is possible to use the stem cells without culture expansion. Caplan also describes a way to isolate stem cells. Although that work was developed from bone marrow isolation, subsequent observations have shown that pluripotent cells are present and can be isolated from nearly all tissues. Particular attention has been attended to isolation from adipose tissue, but the abundance and availability of placental tissue has also garnered a huge interest because of its ready supply.

A major technological hurdle to producing a safe allogeneic composition with viable cells has been the need to approach a fraction of risk approaching zero by removing all antigenic properties that lead to inflammation factors in a separation to yield only a certain stromal cell type. This has proven both difficult and degrading as the quantity of viable cells that can be effectively harvested is greatly diminished by the process itself.

The present invention has yielded a biological composition that is safe and achieves regenerative support and does so in a method that allows the resultant mixture to be recovered from placental tissues wherein the mixture unexpectedly exhibits evidence of regenerative capacity sustaining a legacy, or memory of the lineages from where the acellular biological composition had been associated. This retained ability, or regenerative resonance to support the emergence of new tissue forms including bone and other tissues was independent of mesenchymal cells.

These and other benefits of the present invention and the method of preparing it are described hereinafter.

SUMMARY OF THE INVENTION

A biological composition has a mixture of mechanically selected allogeneic biologic material derived from placental tissues. The mixture has non-whole cellular components including vesicular components and active and inactive components of biological activity, cell fragments, cellular excretions, cellular derivatives, and extracellular matrix components. The mixture including non-whole cell fractions including one or more of exosomes, transcriptosomes, proteasomes, membrane rafts, lipid rafts. The mixture is compatible with biologic function.

The mixture of mechanically selected material is derived from placental tissues. The biological composition preferably has placental particles including derivatives of the amnion, chorion, epithelial layer, and can include non-whole cellular fragments of the umbilical cord and fetal and maternal vessels including Wharton Jelly. Mesenchymal cells derived from amniotic tissue can be added to the mixture derived from placental tissues.

The combination of non-whole cell components with a select number of non-whole cell fractions sustains pluripotency in the cells. In a preferred embodiment, the biological composition is predisposed to demonstrate or support elaboration of active volume or spatial geometry consistent in morphology with host specific tissue and organ geometry. The biological composition extends regenerative significance that compliments or mimics tissue complexity. The mixture is treated in a protectant or cryoprotectant prior to preservation or cryopreservation or freeze drying. The composition can be maintained at ambient temperature prior to freeze drying. The protectant or cryoprotectant creates a physical or electrical or chemical gradient or combination thereof for tissue regeneration. The gradient can have a physical characteristic of modulus or topography, such as charge density, field shape or cryo or chemotaxis tendencies. The gradient can have a chemical characteristic of spatially changing compositions of density or species of functional molecules, wherein the molecules can offer a fixed catalytic function as a co-factor. Also, the gradient can have an electrical characteristic of charge based or pH based or electron affinities that confer metastability in biologic potential.

The placental tissue mixture which is donor derived from a Caesarean section has separation-enhanced non-whole cell fraction vitality including one or more of the following: separating the fractions from cells heightens their vital potency, reversing "arrest" of donor tissue following birth process, responsive molecular coupling, matrix quest in neutralizing inflammation or satience by balancing stimulus for repair. The protectant or cryoprotectant is a polyampholyte. The regenerative resonance occurs in the presence or absence of a refractory response. When using a cryoprotectant, the cryopreservation occurs at a temperature that is sub-freezing wherein the cryopreservation temperature is from 0 degrees C. to −200 degrees C. The protection may also be achieved by non-cryogenic means.

The biological composition's non-whole cellular component also can include organelle fragments and the active and inactive components of biological activity which can also include extants of the human metabolome.

A method of making a biological composition of the present invention has the steps of: collecting, recovering and processing placental tissue from a donor; mechanically separating the cellular or non-cellular components or a combination thereof of placental tissue from surgical C-section; concentrating by centrifugation and filtering; separation by density gradient centrifugation; collecting non-cellular fractions or non-cellular components or a combination thereof of predetermined density; washing the non-whole cellular fractions or non-cellular components or a combination thereof to create the mixture; quantifying concentrations of non-cellular fractions components at a non-zero entity; suspending to a predetermined concentration in a polyampholyte cryoprotectant; freezing the mixture at a predetermined controlled rate; and packaging a placental-derived blend having particles in the size range of 100 to 300 μm of chorion, amnion, umbilical cord matrix, Wharton's Jelly, within the mixture or separate, or in combination. Novel acellular materials including exosomes have been shown to range from 30-120 nm as endocytic membrane-derived vesicles, and have been shown in several reviews that participate in cell-to-cell communication and protein and RNA delivery. These particle size ranges can vary higher or lower depending on the application. At the time of use, the mixture is thawed by immersion in a warm water bath for 2-3 minutes at 37 degrees C., or held in hand until liquid It is diluted in saline without spinning; and then the diluted mixture, with or without the morselized matrix materials being intermixed, can be implanted by packing, injection, scaffolding or any other suitable means into a patient.

Definitions

DNase—deoxyribonuclease is any enzyme that catalyzes the hydrolytic cleavage of phosphodiester linkages in the DNA backbone, thus degrading DNA.

DMEM, DMEM/LG—Dulbecco's Modified Eagle Medium, low glucose. Sterile, with: Low Glucose (1 g/L), Sodium Pyruvate; without: L-glutamine, HEPES (4-(2-hydroxyethyl)-1-piperazineethanesulfonic acid)

DPBS—Dulbecco's Phosphate Buffered Saline.

Cryopreserved—Tissue frozen with the addition of, or in a solution containing, a cryoprotectant agent such as glycerol, or dimethylsulfoxide, or carboxylated poly-1-lysine.

Freeze Dried/Lyophilized—Tissue dehydrated for storage by conversion of the water content of frozen tissue to a gaseous state under vacuum that extracts moisture.

Normal Saline—0.9% Sodium Chloride Solution.

Packing Media—Media used during initial processing and storage of the processed tissue prior to decellularization.

PBS—Phosphate Buffered Saline.

Processing Media—Media used during bone decellularization that may contain DMEM/Low Glucose no phenol red, Human Serum Albumin, Heparin, Gentamicin and DNAse.

BRIEF DESCRIPTION OF THE DRAWINGS

The patent or application file contains at least one drawing/photograph executed in color. Copies of this patent or patent application publication with color drawing(s) will be provided by the Office upon request and payment of the necessary fee.

The invention will be described by way of example and with reference to the accompanying drawings in which.

DETAILED DESCRIPTION OF THE INVENTION

With reference to the present invention which is a tissue regenerative biological composition made from placental material including derivatives of amnion, chorion, umbilical cord, Wharton's Jelly, it is believed best understood by the methods used to process and recover the biological composition, as illustrated in the FIGS. 1-7.

Figure 1:
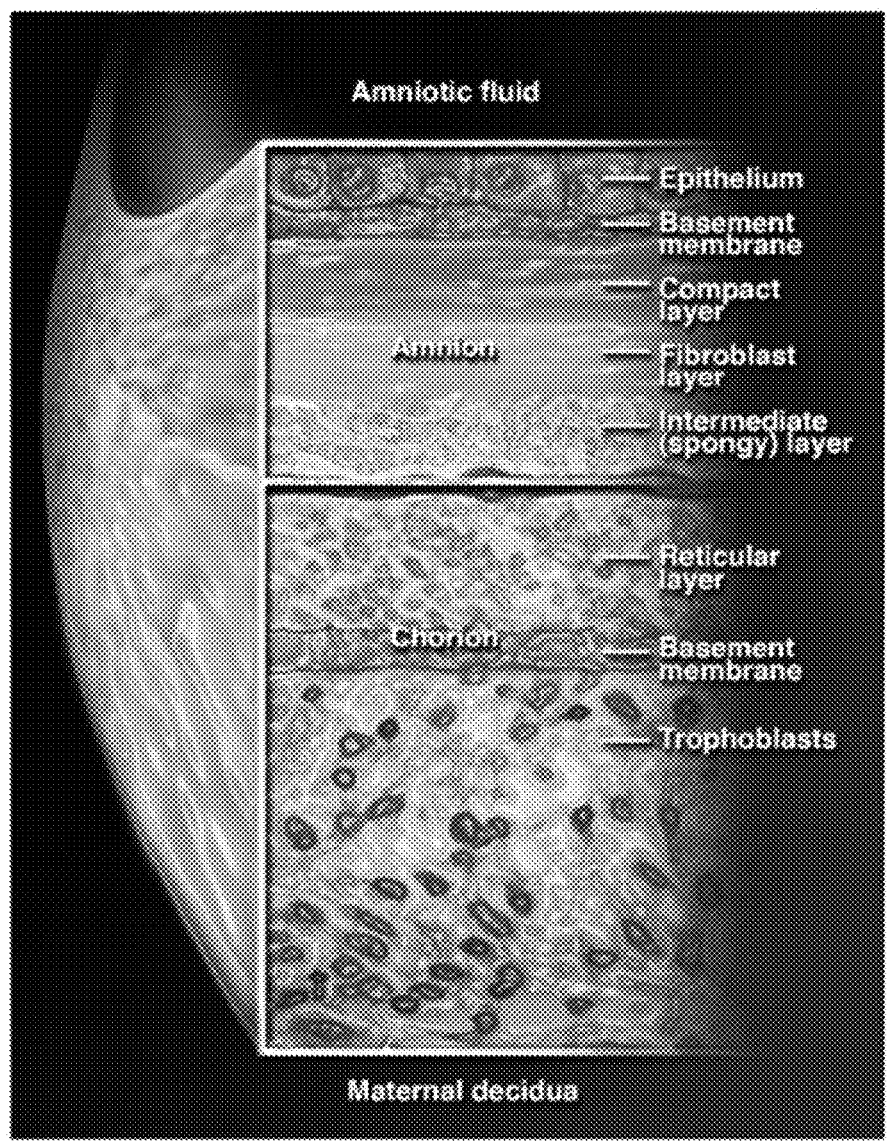
FIG. 1 Depiction of full fetal membranes from placental material, including both amnion and chorion layers from a donor placenta.
Figure 2:
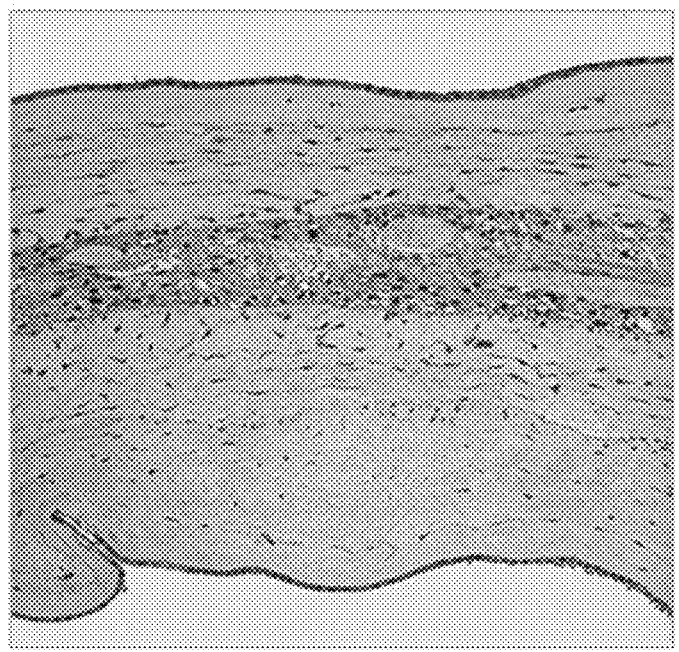
FIG. 2 Photo-micrograph depicting both the amnion and chorion layers of fetal membrane.
Figure 3:
FIG. 3 shows a photomicrograph of the amnion separated from the chorion layer.
Figure 4:
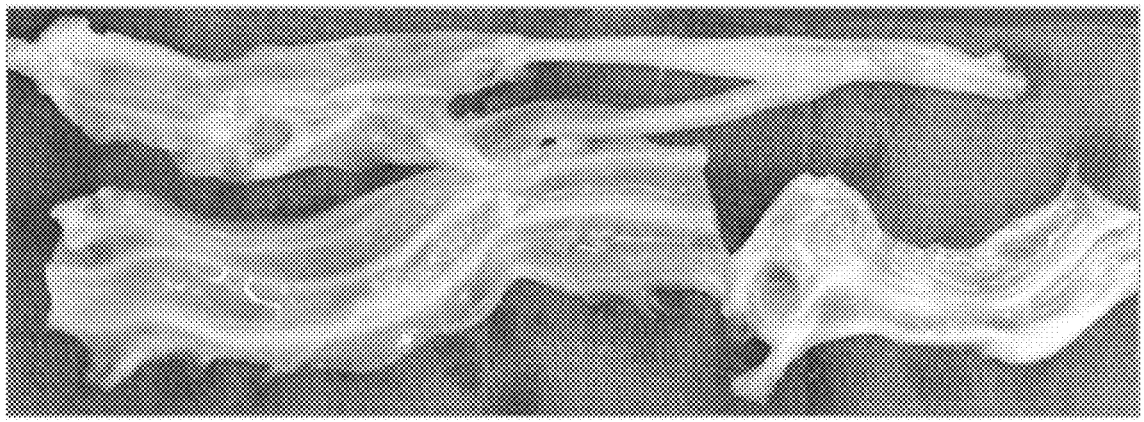
FIG. 4 shows umbilical cord tissue reduced to its membrane and scraped clean of connective tissue.

The first steps are to collect, recover and process placental materials from a C-section donor of a live birth. To do this, the placenta is removed and collected aseptically following the birth and the resultant material is covered by cold media. This also can include recovery of amniotic fluid as shown in FIG. 3 and the cleaned and scraped umbilical cord tissue shown in FIG. 4.

Figure 5:
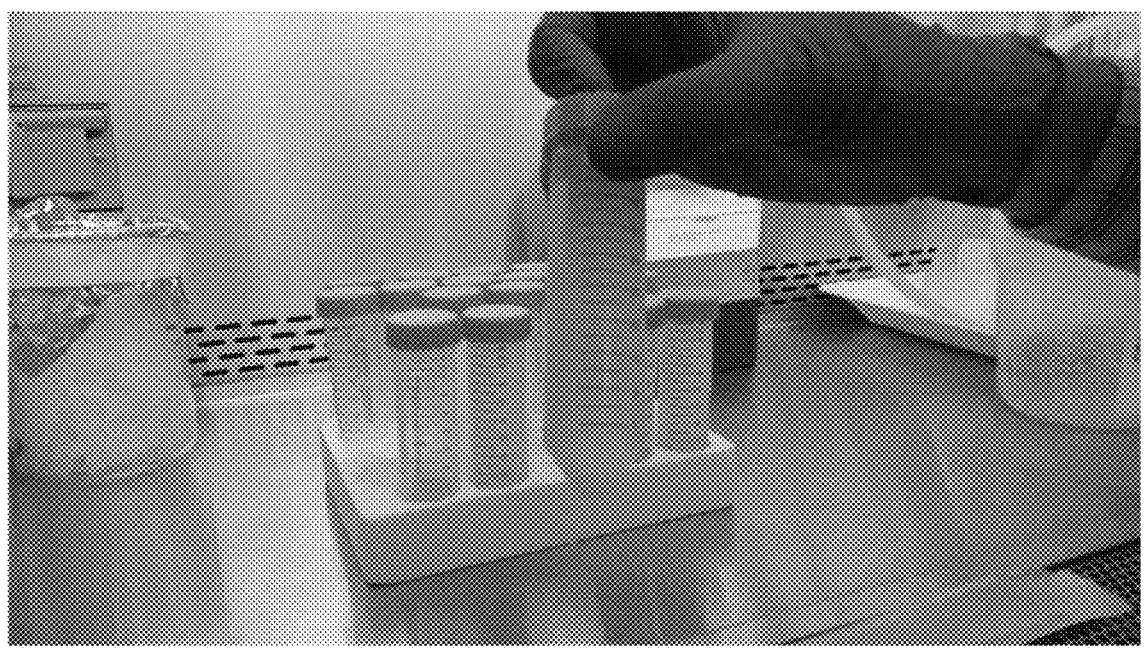
FIG. 5 is a photograph showing plain amniotic fluid after filtration.
Figure 6:
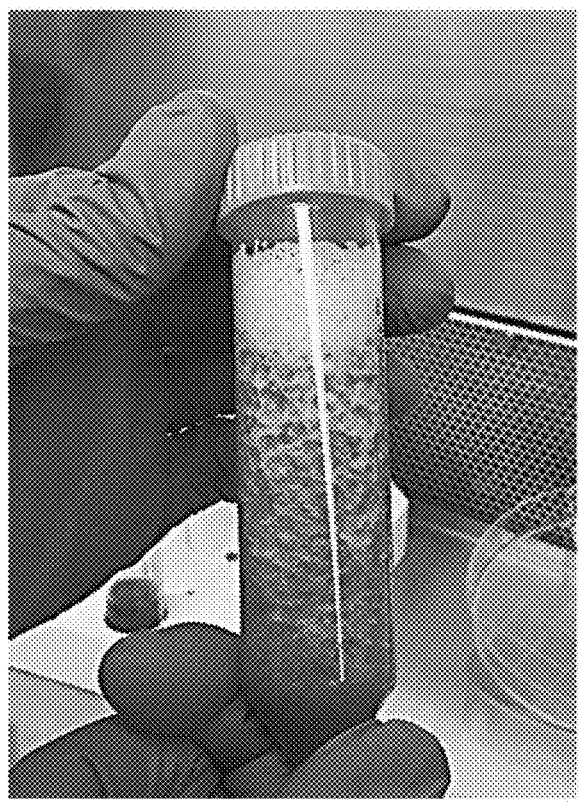
FIG. 6 shows a photograph of the placental material; e.g. placenta, chorion, amniotic membrane, umbilical cord or a mixture of these after being ground and immersed in media.

After each subsequent sieving of the placental material, exosomes can potentially be recovered from the cold media, but also from incubation of micronized tissue with media as well as from the amniotic fluid. The decanted fluid, containing the mixture with whole cells is collected and put into a collection jar. When the next three cycles are complete and the decanted fluid is all placed in the collection jar commingling the fluids to form a decanted fluid. Then the centrifugation of the combined decanted fluid occurs by placing the fluid in a number of 250-ml conical tubes using a 100-ml pipette. The centrifuge is programmed to 280×g for 10 minutes at room temperature, preferably about 20 degrees C., or approximately at normal room temperature. The fluid is passed through a blood filter to further remove any bone or spicules or clumps from the suspended cells. This completes the step of centrifuging and filtering. At this point, as shown in FIG. 5, the mixture including whole cells has been separated from the soft tissue and the remaining macerated and fibrous tissue is discarded.

Typically, non-whole cell fragments, or membrane components have a diameter of 40-100 nm and can be separated within a density of 1.13-1.19 g/mL in a sucrose solution, and can be sedimented by centrifugation at 100,000 g. In fact, these fragments, or cell fractions, or microvesicles, have been collectively referred to as exosomes. Ranging in size from 20-1000 nm in diameter, they have been similarly referred to as nanoparticles, microparticles, shedding microvesicles, apoptotic blebs, and human endogenous retroviral particles. There are few firm criteria distinguishing one type of microvesicle from the other.

Following removal of the cell fraction, the supernatant is further filtered through 0.45 and 0.2 μm filters. Exosomes are further collected and separated within the suspension in multiple centrifugation steps with increasing centrifugal strength to sequentially pellet cells (300 g), microvesicles (10,000 g) and ultimately exosomes (100,000 g). Cells are deliberately removed to achieve the non-whole cell fragments and microvesicles.

Subsequent separation using density gradient-based isolation, using sucrose or commercially available prep can be applied to obtain more pure exosome preparations. Recent reports encouraging the use of iodixanol-based gradients for improved separation of exosomes from viruses and small apoptotic bodies are considerations left open to be adopted or adapted in refinement. Differing from sucrose, iodixanol forms iso-osmotic solutions at all densities, thus better preserving the size of the vesicles in the gradient, and both technologies are available to best isolation technology. In addition to these traditional isolation techniques, easy-to-use precipitation solutions, such as EXOQUICK™ and TOTAL EXOSOME ISOLATION™ (TEI), that have been commercialized reduce the need for expensive equipment or technical know-how. Although their mode-of-action has not been disclosed or validated, these kits are commonly used.

Once the mixture is completed, the method can include additional steps. This leads to the use of a material composition, blends of materials shown in FIG. 6, preferably from the same donor.

Figure 7:
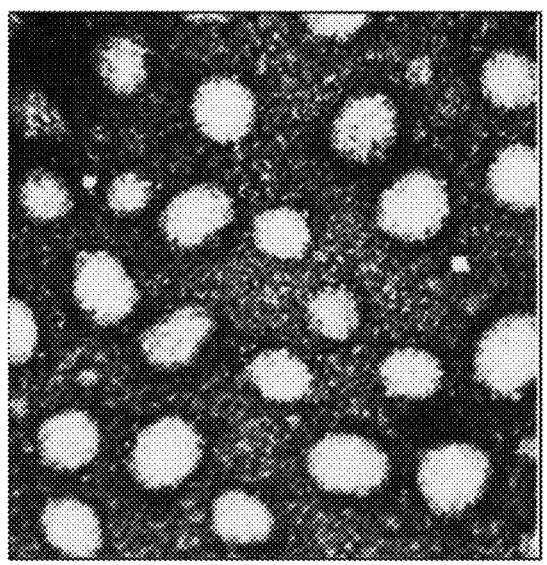
FIG. 7 shows a pair of views of non-whole cell material that can be derived from supernatant of placental material recovery; the resultant material after centrifuging showing the non-whole cell fraction interface layer, including exosomes.
Figure 7:
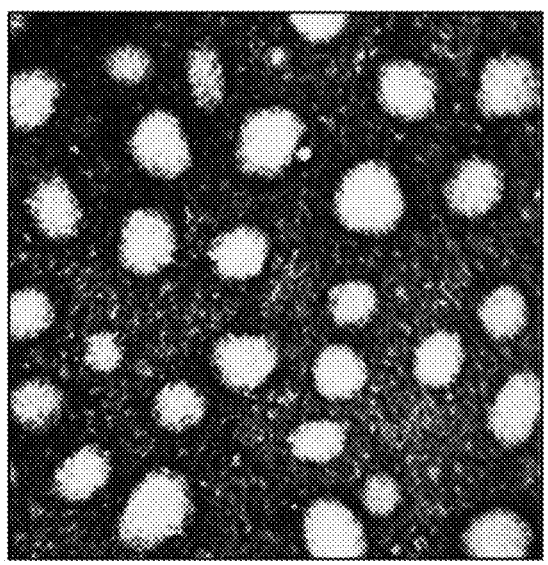

When the mixture is prepared, it can have whole cells or even no whole cells, but will have the mechanically selected non-whole cellular components including vesicular components and active and inactive components of biological activity, cell fragments, cellular excretions, cellular derivatives, and extracellular components from the placental tissues, as shown in FIG. 7.

In one embodiment, the composition includes the whole cells in the mixture. In that embodiment, it is possible to provide bone particles with the mixture either in the mixture or separately to be combined at the time of use.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A method of making a biological composition comprises the steps of:
   collecting, recovering and processing placental tissue from a donor;
   mechanically separating cellular and non-cellular components or combinations thereof of placental tissue;
   concentrating by centrifugation and filtering to form a suspension of the cellular and non-cellular components;
   separating by density gradient centrifugation to form a cell pellet of the cellular components and a supernatant of the non-cellular components wherein the cellular components in the cell pellet are separated from the supernatant and removed and wherein the supernatant is further consisting of filtering through a 0.45 micron filter;
   collecting non-cellular fractions or non-cellular components or combinations thereof of predetermined density by increasing centrifugation strength;
   washing the non-cellular fractions or non-cellular components or combinations thereof;
   quantifying the non-cellular fractions or non-cellular components or combinations thereof separated by density gradient concentration is greater than zero;
   suspending the non-cellular fractions or non-cellular components or combinations thereof to a concentration with a blend of collected, recovered and processed placental tissue and bone particles to create a mixture in a cryoprotectant consisting of a polyampholyte cryoprotectant to create a biological composition, wherein the bone particles having a size range of 100 to 300 µm of demineralized cortical bone, mineralized cortical bone and mineralized cancellous bone intermixed with the non-cellular fractions or non-cellular components; and
   freezing the biological composition at a controlled rate.

2. The method of preparing the biological composition for use made according to the method of claim 1 by the steps of:
   thawing the biological composition;
   diluting the thawed biological composition in saline without spinning; and
   implanting the diluted biological composition with the blend of additional tissue being intermixed by packing, injection or any other suitable means into a patient.

3. The method of preparing the biological composition for use made according to the method of claim 2 wherein the step of thawing the biological composition occurs at a temperature of 37 degrees C. for 2 to 3 minutes in a warm water bath.

4. The method of making the biological composition of claim 1 further consists of the step of adding a quantity of whole cells to the non-cellular fractions or non-cellular components or combinations to a concentration with the blend of collected, recovered and processed placental tissue and bone particles in the polyampholyte cryoprotectant to create the biological composition.

5. A method of making a biological composition comprises the steps of:
   mechanically separating cellular and non-cellular components or combinations thereof of placental tissue;
   concentrating by centrifugation and filtering to form a suspension of the cellular and non-cellular components;
   separating by density gradient centrifugation to form a cell pellet of the cellular components and a supernatant of the non-cellular components wherein the cellular components in the cell pellet are separated from the supernatant and removed and wherein the supernatant is further consisting of filtering through a 0.45 micron filter;
   collecting non-cellular fractions or non-cellular components or combinations thereof of predetermined density by increasing centrifugation strength;
   washing the non-cellular fractions or non-cellular components or combinations thereof;
   quantifying the non-cellular fractions or non-cellular components or combinations thereof separated by density gradient concentration is greater than zero;
   suspending the non-cellular fractions or non-cellular components or combinations thereof to a concentration with a blend of collected and processed placental tissue to create a mixture in a cryoprotectant consisting of a polyampholyte cryoprotectant to form a biological composition; and
   freezing the biological composition at a controlled rate.

6. The method of preparing the biological composition for use made according to the method of claim 5 by the steps of:
   thawing the biological composition;
   diluting the thawed biological composition in saline without spinning; and
   implanting the diluted biological composition by packing, injection or any other suitable means into a patient.

7. The method of preparing the biological composition for use made according to the method of claim 6 wherein the step of thawing the biological composition occurs at a temperature of 37 degrees C. for 2 to 3 minutes in a warm water bath.

8. The method of making the biological composition of claim 5 further consists of the step of adding a quantity of whole cells to the non-cellular fractions or non-cellular components or combinations to a concentration with the blend of collected, recovered and processed placental tissue in the polyampholyte cryoprotectant to create the biological composition.

9. A method of making a biological composition comprises the steps of:
  collecting, recovering and processing placental tissue from a donor;
  mechanically separating cellular and non-cellular components or combinations thereof of placental tissue;
  concentrating by centrifugation and filtering to form a suspension of the cellular and non-cellular components;
  separating by density gradient centrifugation to form a cell pellet of the cellular components and a supernatant of the non-cellular components wherein the cellular components in the cell pellet are separated from the supernatant and removed and wherein the supernatant is further consisting of filtering through a 0.45 micron filter;
  collecting non-cellular fractions or non-cellular components or combinations thereof of predetermined density by increasing centrifugation strength;
  washing the non-cellular fractions or non-cellular components or combinations thereof;
  quantifying the non-cellular fractions or non-cellular components or combinations thereof separated by density gradient concentration is greater than zero;
  suspending the non-cellular fractions or non-cellular components or combinations thereof to a concentration with a blend of collected, recovered and processed placental tissue and bone particles to create a mixture in a cryoprotectant consisting of a polyampholyte cryoprotectant to create a biological composition, wherein the bone particles having a size range of 100 to 300 μm of demineralized cortical bone, mineralized cortical bone and mineralized cancellous bone intermixed with the non-cellular fractions or non-cellular components; and
  freeze-drying the biological composition.

10. The method of preparing the biological composition for use of claim 9 further consists of the steps of:
  diluting the biological composition in saline without spinning; and
  implanting the diluted biological composition with the blend of additional tissue being intermixed by packing, injection or any other suitable means into a patient.

11. The method of making the biological composition of claim 9 further consists of the step of adding a quantity of whole cells to the non-cellular fractions or non-cellular components or combinations to a concentration with the blend of collected, recovered and processed placental tissue in the polyampholyte cryoprotectant to create the biological composition.

12. A method of making a biological composition comprises the steps of:
  mechanically separating cellular and non-cellular components or combinations thereof of placental tissue;
  concentrating by centrifugation and filtering to form a suspension of the cellular and non-cellular components;
  separating by density gradient centrifugation to form a cell pellet of the cellular components and a supernatant of the non-cellular components wherein the cellular components in the cell pellet are separated from the supernatant and removed and wherein the supernatant is further consisting of filtering through a 0.45 micron filter;
  collecting non-cellular fractions or non-cellular components or combinations thereof of predetermined density by increasing centrifugation strength;
  washing the non-cellular fractions or non-cellular components or combinations thereof;
  quantifying the non-cellular fractions or non-cellular components or combinations thereof separated by density gradient concentration is greater than zero;
  suspending the non-cellular fractions or non-cellular components or combinations thereof to a concentration with a blend of collected and processed placental tissue to create a mixture in a cryoprotectant consisting of a polyampholyte cryoprotectant to form a biological composition; and
  freeze-drying the biological composition.

13. The method of preparing the biological composition for use of claim 12 further consists of the steps of:
  diluting the biological composition in saline without spinning; and
  implanting the diluted biological composition with the blend of additional tissue being intermixed by packing, injection or any other suitable means into a patient.

14. The method of making the biological composition of claim 12 further consists of the step of adding a quantity of whole cells to the non-cellular fractions or non-cellular components or combinations to a concentration with the blend of collected, recovered and processed placental tissue in the polyampholyte cryoprotectant to create the biological composition.

* * * * *